United States Patent [19]

Putral et al.

[11] 4,283,370

[45] Aug. 11, 1981

[54] METHOD OF QUANTITATIVELY SEPARATING URANIUM FROM SPECIMENS OF NATURAL WATER BY SORPTION ON SILICA

[75] Inventors: Alexander Putral; Klaus Schwochau, both of Jülich, Fed. Rep. of Germany

[73] Assignee: Kernforschungsanlage Jülich, Gesellschaft mit beschränkter Haftung, Jülich, Fed. Rep. of Germany

[21] Appl. No.: 903,079

[22] Filed: May 5, 1978

[30] Foreign Application Priority Data

May 10, 1977 [DE] Fed. Rep. of Germany ....... 2720867

[51] Int. Cl.$^3$ .......................... C22B 60/02; C02B 1/28
[52] U.S. Cl. .......................................... 423/6; 210/684
[58] Field of Search ............. 423/6; 210/21, 24, 38 C, 210/37 R, 37 B; 73/63.1, 53

[56] References Cited

U.S. PATENT DOCUMENTS

| | | | |
|---|---|---|---|
| 2,885,258 | 5/1959 | Bain | 423/6 |
| 2,966,393 | 12/1960 | Kember | 423/6 |

FOREIGN PATENT DOCUMENTS

| | | | |
|---|---|---|---|
| 738910 | 7/1966 | Canada | 423/6 |
| 49-14443 | 4/1974 | Japan | 423/6 |

OTHER PUBLICATIONS

Zaki, Z., *Anorg. Allg. Chem.*, j360; 208–212, "Studies on the Uptake of Uranium (VI) on Silica Gel," 1968.

Sulcek et al., *Analytica Chemica Acta*, "The Use of Silica Gel for the Separation of Traces of Uranium," 1970, pp. 335–344.

French et al., *Transactions of the Faraday Society*, "The Magnetochemistry of Adsorption of Ions from Solution," 1956, pp. 996–998.

*Primary Examiner*—Richard E. Schafer
*Attorney, Agent, or Firm*—Becker & Becker, Inc.

[57] ABSTRACT

A method of quantitatively separating uranium from specimens of natural water, especially sea water or from solutions which as to their composition are comparable to such specimens, while silica gel is provided for adsorbing the uranium. The liquid of the specimens or solution is conveyed over granular silica gel having an average grain diameter not exceeding 0.5 mm. The through-flow speed is so selected that the contact time period for the liquid with the silica gel amounts to at least 50 seconds; whereupon the uranium adsorbed on the silica gel is separated therefrom by elutriation with at least 0.1 normal oxidizing mineral acid. The volume of the elutriate utilized, should amount to at least twice the volume of the silica gel, and this proportion of the elutriate should, if possible, not be exceeded.

3 Claims, No Drawings

METHOD OF QUANTITATIVELY SEPARATING URANIUM FROM SPECIMENS OF NATURAL WATER BY SORPTION ON SILICA

The present invention relates to a method of quantitatively separating uranium from specimens of natural water, especially sea water, provided for the quantitative determination of the uranium, or from solutions comparable as to their composition to said specimens, while silica gel is provided for adsorption of the uranium.

The possibility of being able quantitatively to determine the uranium content in natural water is one of the necessary requirements for research work in the field of recovering uranium from sea water and also for control measurements in connection with the recovery of uranium. Inasmuch as in this connection the measurement of very minute concentrations of uranium is involved—for instance only about 3.3 $\mu g$ of uranium is contained in 1 kg of sea water—it will be appreciated that on one hand very precise measuring methods are required in order to be able precisely to prove said minute quantities of uranium in a sufficiently precise manner. Inasmuch as in natural water, in addition to uranium, also foreign ions are present, which harmfully affect the proof of the presence of uranium, on one hand, a pretreatment of the specimen liquid is necessary which is provided for the quantitative measurement. Thus, for instance, in the sea water a quantity of foreign ions is dissolved which amounts to about $10^7$ times the quantity of uranium complex bound as $[UO_2(CO_3)_3]^{-4}$. Therefore, efforts are made to separate the uranium from the specimen liquid while as much as possible separating the uranium from the quantity of foreign ions.

From Anal. Chim. Acta 53 (1971) Page 343, a method of quantitatively ascertaining uranium from natural water has become known, according to which the specimen liquid is first supplemented by an addition of acids and is then evaporated to a dry condition (Trockene), whereupon the residue with hydrochloric acid is dissolved by adding water. The solution is then filtered and the filtrate is passed over silica gel after the addition of complex formers passed to bind interfering foreign ions. Aside from the fact that this known method is rather expensive, this method has the drawback that it cannot be used in connection with sea water in view of the high salt content thereof.

It is, therefore, an object of the present invention to provide a method which in a simple manner makes possible a separation of the uranium from the specimen liquid of a natural water, especially of sea water or of a solution which is comparable to the specimen liquid of natural water, while at the same time the uranium will be separated from the major portion of the interfering foreign ions so that the second solution formed in this connection, in which the uranium is present in a higher concentration with regard to the starting liquid, can be used for the quantitative ascertainment of the uranium by means of known measuring methods.

The problem underlying the present invention has been solved with a method of the above mentioned general type by passing the specimen liquid over granular silica gel of an average grain diameter of a maximum of 0.5 mm while the through-flow speed is so selected that the contact time for the specimen liquid in the silica gel will amount to at least 50 seconds. Thereupon the uranium adsorbed on the silica gel is detached therefrom by elutriation by means of at least 0.1 normal oxidizing mineral acid, in which connection the utilized elutriation substance as far as possible amounts to at least twice the volume of the silica gel, but possibly should not materially exceed twice the volume of the silica gel. By contact time is meant the time which a volume of liquid corresponding to the volume of the adsorbing bed requires for passing through said adsorbing bed.

The present invention is based on the surprising finding that the quantitative adsorption of the uranium of silica gel is not even affected by a high excess of foreign ions as it is present for instance in sea water. The separation of uranium from foreign ions is not complete, and therefore no complete selective adsorption of the uranium can be mentioned. The enrichment of the uranium relative to the foreign ions, however, amounts, when utilizing the method according to the invention to sea water, to a plurality of orders of magnitudes so that the elutriate formed in conformity with the present invention contains uranium and foreign ions at a quantity ratio which makes possible the utilization of known analyzing methods. An addition of chemicals for masking interfering ions, is therefore not necessary with the method according to the invention.

The method according to the invention is applicable to slight acidic, neutral or slightly alkaline solutions, even when they contain a higher percentage of salt. Also natural variations in the salt concentration and the pH value have no influence upon the adsorption behavior of the silica gel. In this connection, uranium may be present in the specimen solution in the form of tricarbonate uranylate—anion—as well as in the form of uranyl kations. The uranium concentration in the solution may in this connection amount to from 0.1 to 1000 $\mu g$ per liter solution, while also with 1000 $\mu g$ uranium per liter the separation of uranium can still be carried out quantitatively. It is, of course, understood that the method according to the invention can be utilized also with industrially obtained aqueous solutions having a uranium content which corresponds to the above mentioned values.

In this connection, it is expedient when utilizing the method of the invention to convey the specimen liquid over silica gel of an average grain diameter within the range of from 0.2 to 0.5 mm. For carrying out the method of the invention, a quantity of from 0.1 to 1 liter specimen liquid is sufficient, especially when the quantitative ascertainment of the uranium is effected in a fluorometric way.

For purposes of regenerating the silica gel, the latter after the elutriation of the uranium is washed with distilled water until the running-off water reacts neutrally. Subsequently thereto the silica gel may again be utilized and is adapted to be regenerated almost indefinitely.

EXAMPLE 1

For checking the precision of the method according to the invention, the method was utilized with or applied to a series of specimen solutions the composition of which with regard to the quantitatively more important components corresponds to the composition of sea water and which were dotted with different quantities of $Na_4[UO_2(CO_3)_3]$. Aside from the quantity of uranium which results from Column 1 of the table below, the utilized solutions had the following compositions:

| | |
|---|---|
| 28.0 g NaCl | per Liter H₂O distilled |
| 7.0 g MgSO₄ . 7H₂O | " |
| 5.0 g MgCl₂ . 6H₂O | " |
| 1.6 g CaCl₂ . 2H₂O | " |
| 0.2 g NaHCO₃ | " |

Salt concentration: 3.41%. The pH value was set with NaOH to 8.0.

For carrying out the method, one liter of specimen liquid was passed over commercial silica gel 40 (silica gel with an average pore width of 40 Å) which was in a glass column of 12 mm inner diameter. The filling level of the silica gel amounted to 120 mm so that about 13.5 ml (about 9 grams) silica gel 40 was utilized for separating the uranium from the specimen liquid. The diameter of the silica gel particles amounted to from 0.2 to 0.5 mm.

The specimen liquid was introduced from above onto the silica gel while, without pumping or withdrawing the liquid, a throughflow of about 500 ml per hour was obtained. The contact period amounted to about 100 seconds. Prior to the elutriation of the uranium, the column of silica gel was washed with 20 ml distilled water. For the elutriation of the uranium, 30 ml 1 molar nitric acid is passed through the bed of silica gel. The elutriate was evaporated to dry (zur Trockene), the residue was dissolved in 5 ml 1 molar nitric acid, and after liquid-liquid-extraction with methyl-iso-butylketone, the uranium content in 5 ml solution was measured in a fluorometric way. The results of these measurements are set forth in Table 1 below:

TABLE 1

| predetermined uranium concentration [µg/l] | ascertained uranium concentration [µg/l] | Deviation % |
|---|---|---|
| 1000 | 998 | −0.2 |
| 100.0 | 99.9 | −0.1 |
| 10.00 | 10.20 | +2.0 |
| 8.00 | 8.20 | +2.5 |
| 6.00 | 5.90 | −1.7 |
| 4.00 | 3.75 | −6.2 |
| 3.00 | 2.85 | −5.0 |
| 2.00 | 2.05 | +2.5 |
| 1.00 | 1.07 | +7.0 |
| 0.60 | 0.61 | +1.7 |
| 0.30 | 0.28 | −6.7 |
| 0.10 | 0.11 | +10.0 |
| 0.00 | 0.03 | — |

EXAMPLE 2

For ascertaining the reproducibility of the method, uranium was quantitatively determined from a series of specimens of sea water surrounding the island of Helgoland in the North Sea, while the specimens respectively consist of one liter of sea water. The composition of the Helgoland sea water corresponds to the known composition of sea water in the oceans. The separation of the uranium from the specimen liquids as well as the elutriation and the quantitative measurement of uranium was carried out as described in the Example 1. The resulting values of this measuring series are set forth in Table 2 below:

TABLE 2

| Specimen No. | Uranium Concentration [µg/l] |
|---|---|
| 1 | 3.16 |
| 2 | 3.28 |
| 3 | 3.10 |
| 4 | 3.22 |
| 5 | 3.10 |
| 6 | 3.25 |
| 7 | 3.20 |
| 8 | 3.15 |
| 9 | 3.20 |
| 10 | 3.18 |

The average value of the uranium concentration amounts to 3.18 µg/l, the variation coefficient is 1.9%.

For the sake of completeness it may be mentioned that while it has been set forth herein in connection with the method of the present invention that the volume of the utilized elutriate is selected to amount to at least about two times the volume of the utilized silica gel, it is, of course, possible to utilize a considerably greater quantity of elutriate, e.g. 50 or 100 times more. However, since the present invention concerns a method to be utilized in connection with the enrichment of uranium to be recovered from sea water, it would not be meaningful to utilize a greater volume of elutriate than is necessary. Experience has shown that in connection with the present invention it will suffice to so select the quantity of the elutriate that its volume amounts to about twice the volume of the silica gel.

It is, of course, to be understood that the present invention is by no means limited to the specific examples set forth above, but also comprises any modifications within the scope of the appended claims.

What we claim is:

1. A method of quantitatively separating uranium anions from test liquids either simulating natural sea water or test liquids of natural sea water, which method includes, in combination, the steps of: passing the test liquid directly without pretreatment over granular silica gel having an average grain diameter not exceeding 0.5 mm, while so selecting a through-flow speed of said test liquid that the contact time period for the said test liquid with said silica gel amounts to at least 50 seconds, and subsequently separating the uranium anions quantitatively adsorbed on said silica gel from the latter by elutriation with at least 0.1 normal oxidizing mineral acid, the volume of the utilized elutriate being selected to amount to at least about two times the volume of said silica gel.

2. A method in combination according to claim 1, which includes said passing of test liquid is passed over silica gel having an average grain diameter within the range of from 0.2 to 0.5 mm.

3. A method in combination according to claim 1, which includes the quantity of the test liquid in amounts to from 0.1 to 1 liter.

* * * * *